United States Patent
Keech et al.

(10) Patent No.: US 10,512,756 B2
(45) Date of Patent: Dec. 24, 2019

(54) SIZING CATHETERS

(71) Applicant: CARDIAC DIMENSIONS PTY. LTD., Kirkland, WA (US)

(72) Inventors: Evan M. Keech, Shoreline, WA (US); Lucas S. Gordon, Vashon, WA (US)

(73) Assignee: Cardiac Dimensions Pty. Ltd., Kirkland, WA (US)

( * ) Notice: Subject to any disclaimer, the term of this patent is extended or adjusted under 35 U.S.C. 154(b) by 178 days.

(21) Appl. No.: 15/405,117

(22) Filed: Jan. 12, 2017

(65) Prior Publication Data

US 2018/0193597 A1   Jul. 12, 2018

(51) Int. Cl.
| | |
|---|---|
| *A61M 25/01* | (2006.01) |
| *A61B 6/00* | (2006.01) |
| *A61B 6/12* | (2006.01) |
| *A61M 39/06* | (2006.01) |
| *A61M 25/00* | (2006.01) |
| *B29C 63/00* | (2006.01) |
| *B29L 31/00* | (2006.01) |
| *B29C 63/42* | (2006.01) |

(52) U.S. Cl.
CPC .......... *A61M 25/0108* (2013.01); *A61B 6/12* (2013.01); *A61B 6/485* (2013.01); *A61M 25/0009* (2013.01); *A61M 39/06* (2013.01); *A61M 2205/0216* (2013.01); *B29C 63/0069* (2013.01); *B29C 63/42* (2013.01); *B29L 2031/7542* (2013.01)

(58) Field of Classification Search
CPC ............ A61M 25/0108; A61M 25/009; A61M 52/001; A61M 2205/0216; A61B 6/12; A61B 6/485; A61B 2/82; A61B 5/107; B29C 63/0069; B29C 63/18; B29C 66/545; B29L 2031/7542
See application file for complete search history.

(56) References Cited

U.S. PATENT DOCUMENTS

| | | |
|---|---|---|
| 3,618,614 A | 11/1971 | Flynn |
| 4,279,252 A | 7/1981 | Martin |
| 4,385,635 A | 5/1983 | Ruiz |
| 4,571,240 A | 2/1986 | Samson et al. |
| 4,938,220 A | 7/1990 | Mueller, Jr. |
| 5,045,071 A | 9/1991 | McCormick et al. |
| 6,036,682 A | 3/2000 | Lange et al. |
| 6,078,832 A | 6/2000 | Lenker et al. |

(Continued)

FOREIGN PATENT DOCUMENTS

WO    WO2015/153599 A1    10/2015

OTHER PUBLICATIONS

International Search Report and Written Opinion ; PCT/US2018/12296; 7 pages; dated Mar. 20, 2018.

*Primary Examiner* — Paula J Stice
(74) *Attorney, Agent, or Firm* — Shay Glenn LLP

(57) ABSTRACT

Sizing catheters that include an inner member and an outer member. The inner member includes an elongate shaft and a plurality of radiopaque markers spaced axially from each other and secured to an outer surface of the shaft, the span of radiopaque markers defining a first portion of the inner member. The outer member that is disposed snugly around and in substantial contact with the inner member along at least the first portion of the inner member.

15 Claims, 2 Drawing Sheets

(56) References Cited

U.S. PATENT DOCUMENTS

| | | | | |
|---|---|---|---|---|
| 6,179,811 | B1* | 1/2001 | Fugoso | A61M 25/0108 |
| | | | | 604/529 |
| 6,210,338 | B1 | 4/2001 | Afremov et al. | |
| 6,241,678 | B1 | 6/2001 | Afremov et al. | |
| 9,192,500 | B1* | 11/2015 | Longo | A61B 90/00 |
| 2002/0165600 | A1* | 11/2002 | Banas | A61F 2/91 |
| | | | | 623/1.11 |
| 2008/0200874 | A1* | 8/2008 | Ferry | A61M 25/0045 |
| | | | | 604/103.1 |
| 2009/0326560 | A1 | 12/2009 | Lampropoulos et al. | |
| 2011/0172644 | A1* | 7/2011 | Zanoni | A61L 29/18 |
| | | | | 604/529 |
| 2014/0058251 | A1* | 2/2014 | Stigall | A61B 5/1076 |
| | | | | 600/424 |

* cited by examiner

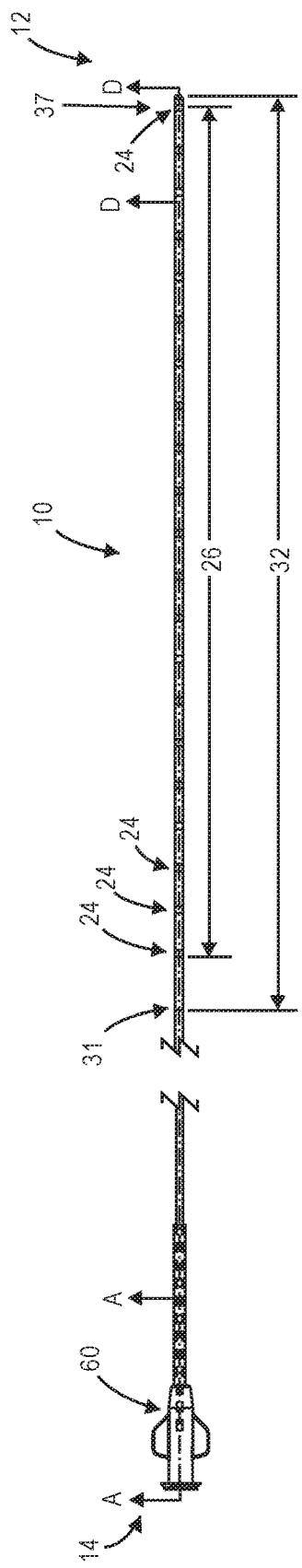
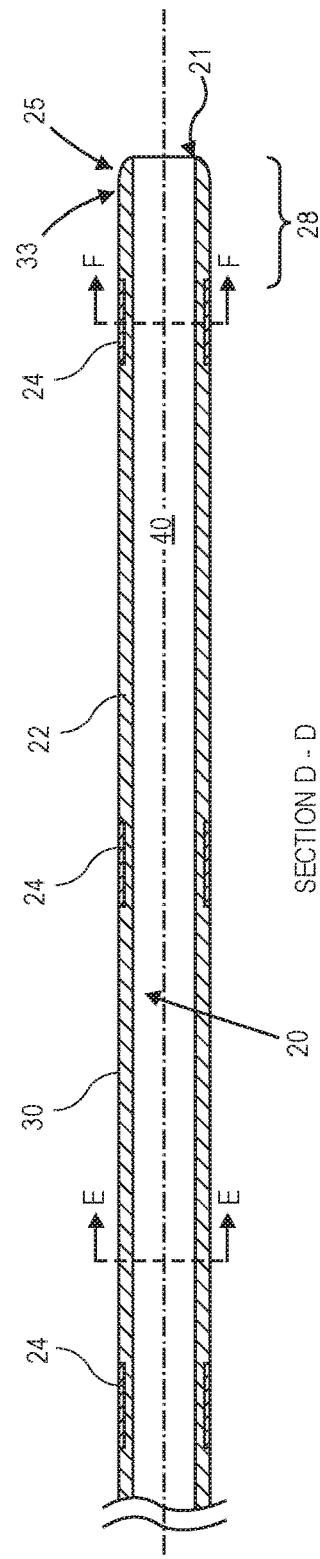
FIG. 1
FIG. 2

SECTION E - E

SECTION F - F

SECTION A - A

SIZING CATHETERS

INCORPORATION BY REFERENCE

All publications and patent applications mentioned in this specification are herein incorporated by reference to the same extent as if each individual publication or patent application was specifically and individually indicated to be incorporated by reference.

BACKGROUND

Catheters that incorporate a plurality of spaced radiopaque markers can be used to, when positioned inside a patient and visualized using X-ray based techniques such as fluoroscopy, determine one or more dimensions of a vessel in which it is placed (e.g., diameter), or establish a magnification factor that the X-ray is using. An exemplary use of such a catheter can be to determine one or more dimensions of a vessel to help select an appropriately sized implant that is to be implanted within the vessel. These catheters may be referred to herein as sizing catheters or scaling catheters.

Sizing catheters that incorporate a plurality of axially spaced radiopaque markers are known. Standard sizing or scaling catheters incorporate the plurality of axially spaced radiopaque markers in such a way that the markers are disposed on the outside of an elongate shaft, such that the markers form an outer surface of the catheter at the locations of the markers. There is a risk that after the catheter has been advanced into the subject, the markers may become dislodged or disassociated from the elongate shaft, and remain inside the patient, subjecting the patient to serious complications. For example, the catheter may be advanced along a somewhat or very tortuous path, bending the catheter, which may result in forces being applied at the locations where the markers are coupled to the elongate shaft, which may cause the markers to become disassociated from the shaft.

Additionally, to deliver the sizing catheter to a target location inside the patient, sizing catheters may be advanced through an introducer catheter or sheath, which can include a hemostasis valve at the proximal end of the introducer. As the sizing catheter is advanced through the hemostasis valve, forces from the valve on the sizing catheter and radiopaque markers can destabilize the marker/shaft interface, thus increasing the likelihood that the markers can become dislodged inside the patient.

Sizing catheters and scaling catheters are needed that eliminate the risk that the plurality of radiopaque markers become dislodged from the catheter and remain in the patient.

SUMMARY OF THE DISCLOSURE

The disclosure relates to sizing catheters.

One aspect of the disclosure is a sizing catheter that includes an inner member comprising a resilient elongate shaft and a plurality of radiopaque markers spaced axially from each other and secured to an outer surface of the elongate shaft, the span of radiopaque markers defining a first portion of the inner member, and an outer member that is disposed snugly around and in substantial contact with the inner member along at least the first portion of the inner member.

In some embodiments a thickness of the outer member is less than 0.01 inches.

In some embodiments the elongate shaft comprises a wall thickness of at least three times the thickness of the outer member.

In some embodiments the elongate shaft and the outer member comprise an elastomeric material.

In some embodiments the elongate shaft comprises a radiopaque material.

In some embodiments the distance between adjacent radiopaque markers is substantially uniform, and optionally from 0.25 to 1.0 inches.

In some embodiments a distal end of the elongate shaft comprises a second portion that extends further distally than a distal end of the outer member.

In some embodiments the distal end of the elongate shaft comprises a decreasing wall thickness.

In some embodiments a distal end of the elongate shaft defines the distal end of the sizing catheter.

In some embodiments the elongate shaft comprises a lumen extending therethrough.

In some embodiments the most distal radiopaque marker has a distal end that is less than 0.2 inches from a distal end of the elongate shaft, and optionally less than 0.2 inches from a distal end of the sizing catheter.

In some embodiments the outer member is disposed within a strain relief member at a proximal region of the catheter.

BRIEF DESCRIPTION OF THE DRAWINGS

FIG. 1 illustrates an exemplary sizing catheter.

FIG. 2 is a sectional view of a distal region of a sizing catheter.

DETAILED DESCRIPTION

The disclosure relates generally to sizing catheters, which may also be referred to as scaling catheters. The sizing catheters herein include a plurality of radiopaque markers that can be visualized using x-ray technologies such as fluoroscopy.

Figure 3:
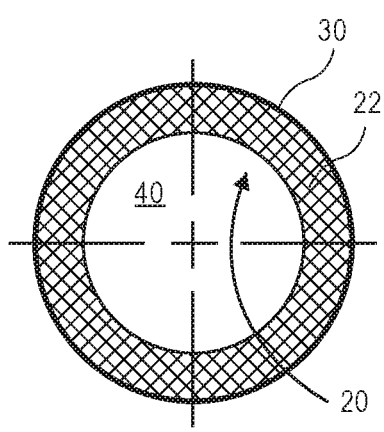
FIG. 3 is a sectional view of a sizing catheter, wherein the section does not include a radiopaque marker.
Figure 4:
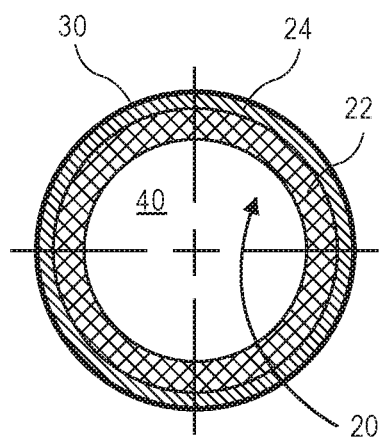
FIG. 4 is a sectional view of a sizing catheter, wherein the section includes a radiopaque marker.
Figure 5:
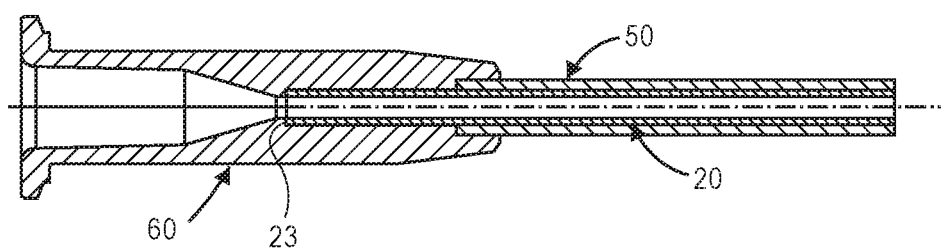
FIG. 5 is a sectional view of a proximal end of an exemplary sizing catheter.

FIGS. 1-5 illustrate an exemplary sizing catheter. FIG. 1 is a side view of catheter 10, which has distal end 12 and proximal end 14. FIG. 2 illustrates Section D-D of catheter 10, which is shown in FIG. 1, and which includes distal end 12. FIG. 3 illustrates Section E-E shown in FIG. 2, while FIG. 4 illustrates Section F-F shown in FIG. 2. FIG. 5 illustrates a proximal region of catheter 10, including proximal end 14.

As shown in FIGS. 1-4, sizing catheter 10 includes inner member 20 and outer member 30. Inner member 20 includes resilient elongate shaft 22 and a plurality of radiopaque markers 24 axially spaced from each other along elongate shaft 22. The plurality of radiopaque markers 24 are secured to an outer surface of elongate shaft 22, such as by known swaging processes. The axial span of the plurality of radiopaque markers 24 defines first portion 26 of inner member 20.

As set forth above, there is a chance that any of the plurality of radiopaque markers may become dislodged while catheter 10 is being advanced into the patient. To minimize, and possibly eliminate, this risk, catheter 10 also includes outer member 30 that is disposed snugly around and in substantial contact with inner member 20 along at least first portion 26 of inner member 20. Outer member 30 extends over all of the plurality of radiopaque markers 24, and in this embodiment has length 32, as can be seen in FIG. 1. Outer member 30 acts as a cover to inner member 20, helping prevent the plurality of radiopaque from becoming dislodged in use. For example, as catheter 10 is advanced through a hemostasis valve, outer member 30 receives the direct forces from the valve, eliminating the forces applied directly from the valve to the radiopaque markers. Additionally, as catheter 10 bends while advancing it inside the patient, outer member 30, by being disposed snugly around and in substantial contact with inner member 20 along the span of radiopaque markers, prevents the plurality of radiopaque markers from being dislodged and remaining in the patient.

FIG. 3 shows Section E-E from FIG. 2, in which inner member 20 does not include a radiopaque marker 24. FIG. 3 shows outer member 30 disposed snugly around and in contact with elongate shaft 22. FIG. 4 show Section F-F from FIG. 2, in which inner member 20 includes a radiopaque marker 24. FIG. 4 shows outer member 30 disposed snugly around inner member 20, which includes elongate shaft 22 and a radiopaque marker 24 secured to an outer surface of elongate shaft 22.

Length 32 of outer member 30 is slightly greater than the axial span of the plurality of radiopaque markers 24 (see FIG. 1). As shown in FIGS. 1 and 2, proximal end 31 of outer member 30 is disposed proximal to the proximal end of the most proximal radiopaque marker, and distal end 33 of the outer member 30 is disposed distal to the distal end of the most distal radiopaque marker. The proximal end of the outer member can be disposed at any location along the inner member from the proximal end of the most proximal radiopaque marker to the proximal end of the inner member. The distal end of the outer member can be disposed at any location along the inner member from the distal end of the most distal radiopaque marker to the distal end of the inner member. Extending the outer member 30 distal to the most distal marker and proximal to the most proximal markers helps prevent the markers from being dislodged.

Outer member 30 is disposed snugly around and in substantial contact with inner member 20 along at least first portion 26 of inner member 20. There may be some discrete locations along first portion 26 for which outer member 30 does not make direct contact with inner member 20, but for most of the length of first portion 26, there is contact between the outer member 30 and inner member 20. For example, as will be described below, some of the outer diameters of the plurality of radiopaque markers may be less than the outer diameter of the elongate shaft 22. In these regions, outer member 30 may not be in direct contact with inner member 20, but outer member 30 is still considered to be in substantial contact with inner member 20 along the first portion 26. The outer member is also disposed snugly around the inner member along at least firs portion 26. In this embodiment outer member 30 is generally cylindrically shaped, even though there may be slightly raised regions at any of the locations of the radiopaque markers due to any of the radiopaque markers having very slightly larger outer diameters than the outer diameter of the elongate shaft. The outer diameter of the any of the radiopaque markers may be very slightly different than the outer diameter of the elongate shaft as a natural consequence of the assembly process, such as by swaging.

One method of manufacturing the sizing catheter in which the outer member becomes disposed snugly around and in substantial contact with the inner member is by, after the plurality of radiopaque markers are secured to the outer surface of the elongate shaft, heat shrinking the outer member around the inner member. The heat shrinking process effectively bonds the elongate shaft of the inner member to the outer member, even if the outer member is not bonded directly to the plurality of radiopaque markers. Thus, even though the outer member may be bonded directly to the inner elongate shaft, but not directly to the plurality of radiopaque markers, the outer member is considered to be disposed snugly around and in substantial contact with the inner member along at least first portion of the inner member.

There may be techniques other than heat shrinking that result in the outer member being disposed snugly around and in substantial contact with the inner member. For example, an adhesive can be applied to at least one of the inner and outer members, and the outer member can then be positioned around the inner member. The adhesive can bond the inner and outer members together.

In some embodiments the plurality of radiopaque markers may be made of a material that allows them to bind to one or more of the inner and outer members during, for example, a heat shrinking process, or other similar manufacturing process. In these instances the outer member would be disposed snugly around and in substantial contact with the inner member. For example, the radiopaque markers may include a polymeric material embedded with radiopaque particles.

The plurality of radiopaque markers are made of, at least, one or more radiopaque materials to enable visualization under an x-ray imaging process. Radiopaque materials that can be used to make the markers are known, mere examples of which include platinum, platinum-iridium, and gold. For example, in some embodiments the radiopaque markers are about 10% platinum and about 0.5% iridium. In some embodiments the radiopaque markers can comprise a polymeric material such as Pebax, and can have radiopaque particles, such as platinum or iridium, embedded therein.

In some embodiments the elongate shaft comprises an elastomeric material such as, without limitation, PEBAX®. The elongate shaft can also include one or more radiopaque materials embedded, or loaded, therein. For example, the elongate shaft can be made from an elastomeric material loaded with, for example without limitation, barium sulfate.

In some embodiments the outer member comprises an elastomeric material, and in some embodiments in which the inner member includes an elastomeric member, the elastomeric materials can be the same, or they may be different. For example, in some embodiments the outer member and the inner member include PEBAX®, and may in fact be the same type of PEBAX®. In some embodiments the elongate shaft includes an elastomeric material with radiopaque materials loaded therein, and the outer member includes the same elastomeric material without radiopaque materials loaded therein. In some embodiments the inner and outer members include elastomeric materials embedded with radiopaque materials.

In some embodiments the elongate shaft has a thickness that is greater than a thickness of the outer member, an example of which is shown in sizing catheter 10. The thickness of the outer member may in some embodiments be relatively thin, compared to the thickness of the elongate shaft, so that the outer member does not significantly increase the outer diameter of the sizing catheter. There may thus be advantageous to the outer member having a thickness that is as small as possible, while still being able to prevent the plurality of radiopaque markers from being dislodged from the inner member. In some embodiments the elongate shaft is at least three times as thick as the outer member, and in some embodiments the elongate shaft is at least five times as thick, and in some embodiments is at least eight times as thick. For example, in some embodiments the elongate shaft has a thickness that is about 0.008 inches to about 0.012 inches, and the outer member has a thickness that is about 0.0008 to about 0.0012 inches. In some exemplary embodiments the thickness of the outer member is less than 0.01 inches.

In some exemplary embodiments the inner diameter of the elongate shaft is 0.035 inches to about 0.055 inches, and the outer diameter of the elongate shaft is about 0.058 inches to about 0.07 inches. In some exemplary embodiments the radiopaque markers each have a thickness that is 0.001 inches to 0.003 inches.

In some embodiments the distance between adjacent radiopaque markers is substantially uniform, such as, for example, between 0.25 and 1.0 inches. In some embodiments the distance between adjacent radiopaque markers is not substantially uniform. In the embodiment in FIGS. 1-5, the distal most radiopaque marker has a distal end that is less than 0.2 inches from the distal end of the elongate shaft, and may be less than 0.1 inch from the distal end of the elongate shaft.

In the exemplary embodiment in FIGS. 1-5, the distal end of the inner member, and specifically the elongate shaft, extends further distally than the distal end of the outer member (see FIG. 2). In other embodiments the outer member can extend as far distally as the inner member. In the embodiment in FIGS. 1-5, the distal end of the elongate shaft defines the distal end of the sizing catheter, although in other embodiments the sizing catheter may include a separate distal tip that is attached to the distal end of the inner member and which defines the distal end of the sizing catheter. An exemplary advantage of not having a separate distal tip attached to the distal end of the sizing catheter is that there is no risk of a separate distal tip separating from the sizing catheter and being left behind in the patient.

In the embodiment in FIGS. 1-5, second portion 28 (see FIG. 2) of the elongate shaft, which extends further distally than the distal end of the outer member, has a region 25 with a decreasing wall thickness in the distal direction. Region 25 has a generally rounded outer surface, and can have a single radius of curvature or not. At least a portion of region 25 can have a radius of curvature of about 0.005 to about 0.045 inches. In this embodiment the sizing catheter does not have a separate atraumatic tip on its distal end, and the generally rounded distal region 25 provides the sizing catheter with a generally atraumatic tip without having to have a separate distal tip attached thereto. In alternative embodiments, however, region 25 can be beveled, or it can be a combination of straight and curved lines.

Sizing catheter also includes lumen 40 defined by the inner surface of elongate shaft 22, as shown in FIG. 2. The lumen can receive and deliver a contract agent from the proximal end of the sizing catheter and out of the distal end of the sizing catheter.

In the embodiment in FIGS. 1-5, sizing catheter 10 includes proximal hub 60 and strain relief member 50, which protects the elongate shaft in the proximal region. As can be seen in FIG. 5, elongate shaft 22 extends through strain relief member 50 and proximal hub 60, with proximal end 14 of sizing catheter 10 being disposed within proximal hub 60. Hub 60 has a channel therein that can receive a contrast agent delivery device, the channel being in fluid communication with lumen 40 defined by the inner surface of elongate shaft 22.

What is claimed is:

1. A sizing catheter, comprising:
   an inner member comprising a resilient elongate shaft and a plurality of radiopaque markers spaced axially from each other and secured to an outer surface of the elongate shaft, a span of the plurality of radiopaque markers defining a first portion of the inner member; and
   an outer member that is configured to be maintained snugly around and in direct contact with the elongate shaft along at least the first portion of the elongate shaft,
   the outer member covering the plurality of radiopaque markers and positioned to prevent the plurality of radiopaque markers from directly contacting surrounding material.

2. The catheter of claim 1, wherein a thickness of the outer member is less than 0.01 inches.

3. The catheter of claim 2, wherein, the elongate shaft comprises a wall thickness that is greater than the thickness of the outer member.

4. The catheter of claim 1, wherein the elongate shaft and the outer member comprise polymeric material.

5. The catheter of claim 1, wherein the elongate shaft comprises a radiopaque material.

6. The catheter of claim 1, wherein a distance between adjacent radiopaque markers is uniform and is between 0.25 and 1.0 inches.

7. The catheter of claim 1, wherein a distal end of the elongate shaft comprises a second portion that extends further distally than a distal end of the outer member.

8. The catheter of claim 7, wherein the second portion comprises a decreasing wall thickness.

9. The catheter of claim 7, wherein a distal end of the second portion of the elongate shaft defines the distal end of the sizing catheter.

10. The catheter of claim 1, wherein the elongate shaft comprises a lumen extending therethrough.

11. The catheter of claim 1, wherein the most distal radiopaque marker has a distal end that is less than 0.2 inches from a distal end of the elongate shaft.

12. The catheter of claim 1, wherein the outer member is disposed within a strain relief member at a proximal region of the catheter.

13. The catheter of claim 1, wherein the elongate shaft has a thickness that is greater than a thickness of the outer member.

14. The catheter of claim 13, wherein the elongate shaft thickness is from 0.008 inches to 0.012 inches.

15. The catheter of claim 13, wherein the outer member thickness is from 0.0008 inches to 0.0012 inches.

* * * * *